US005364269A

United States Patent [19]
Willits et al.

[11] Patent Number: 5,364,269
[45] Date of Patent: Nov. 15, 1994

[54] PARTIAL DENTURE

[75] Inventors: William G. Willits; Thomas P. Schmitt, Jr., both of Norfolk, Va.

[73] Assignee: Lab One Enterprises, L.C., Norfolk, Va.

[21] Appl. No.: 205,782

[22] Filed: Mar. 4, 1994

[51] Int. Cl.$^5$ .......................................... A61C 13/225
[52] U.S. Cl. ................................................... 433/178
[58] Field of Search ............... 433/167, 170, 190, 177, 433/178, 172

[56] References Cited

U.S. PATENT DOCUMENTS

| | | | |
|---|---|---|---|
| 3,412,468 | 11/1968 | Weinstein | 433/170 |
| 4,514,173 | 4/1985 | Re | 433/178 |
| 4,764,115 | 8/1988 | Willits et al. | 433/177 |

*Primary Examiner*—Cary E. O'Connor
*Attorney, Agent, or Firm*—Rhodes, Coats & Bennett

[57] ABSTRACT

The present invention entails a partial denture that is basically constructed of a relatively hard acrylic material and includes a series of artificial teeth implanted along the ridge of the denture. The denture is particularly designed for a certain patient and is provided with at least one existing tooth opening for accommodating certain existing teeth of the patient. Formed about the buccal flange area of the denture and adjacent the existing tooth opening is an elastic retainer strip that is integrally molded with the relatively hard acrylic material of the denture. This elastic retainer strip engages the patient's gum in front of the existing teeth that project through the opening in the denture. On the opposite side of the existing tooth opening and opposite the elastic retainer strip there is provided a metal filler panel that is also bonded or integrally molded with the relatively hard acrylic material. Formed along an upper terminal edge of the metal filler panel is at least one metal tooth rest or clamp. The tooth clamp extends from the upper terminal edge of the metal filler panel and over a portion of at least one existing tooth and wherein the metal clamp turns down and clamps downwardly onto a top portion of at least one existing tooth. The clamping action of the metal clamp assists in retaining the entire denture in a secure and proper position within the patient's mouth, combining the benefits of tooth support in addition to tissue-bone support.

6 Claims, 2 Drawing Sheets

PARTIAL DENTURE

FIELD OF INVENTION

The present invention relates to artificial dentures and more particularly to a partial denture that is designed to accommodate at least one existing tooth of the patient and which is provided with a metal clamp for engaging a portion of that existing tooth for purposes of retaining the denture within the patient's mouth.

BACKGROUND OF THE INVENTION

Partial dentures are very popular and are used by people throughout the world. A principal advantage of a partial denture is that it gives an individual the option of having an artificial denture but yet permits the patient to retain existing healthy teeth. Because partial dentures are relatively inexpensive, patients can from time to time remove unhealthy existing teeth and obtain a new partial denture that takes into account the present state of the patient's existing teeth. One example of a successful partial denture that has been sold throughout the United States is that found in U.S. Pat. No. 4,764,115.

It is always a goal of the dentist or denture practitioner to design and fit a denture with maximum comfort to the patient. That is of course important because the denture is continuously worn by the patient and must be functional at all times.

While partial dentures have met with great success over the years and while partial dentures continue to be in high demand, there is one problem or drawback that confronts all designers or builders of partial dentures. That problem or drawback relates to retention and particularly the design concern for providing a partial denture that maintains a precise fit and which is designed in such a fashion that the partial denture is securely retained in the patient's mouth. In this regard, it is not only important to secure the denture in the patient's mouth and stabilize the denture during difficult eating exercises but it is important to provide retention and securement while still maintaining comfort. Too often, designs that assure good securement do not adequately address the patient's concern for comfort.

Therefore, there has and continues to be a need for a partial denture design that provides a design that lends itself to retention and to securement and at the same time imparts maximum comfort to the patient.

SUMMARY AND OBJECTS OF THE INVENTION

The present invention entails a partial denture that is designed to overcome the drawbacks and disadvantages of partial dentures of the prior art. In particular, the partial denture of the present invention includes a direct and positive clamping arrangement that functions to clamp the partial denture in place within the patient's mouth. The partial denture of the present invention comprises a base formed substantially of a relatively hard acrylic material. However, adjacent an existing tooth opening of the partial denture is provided a metal filler panel that is bonded or otherwise integrally formed with the relatively hard base acrylic material. Along the upper terminal edge of the metal filler panel, there is provided one or more metal tooth clamps that project from the upper terminal edge and over and onto one or more of the patient's existing teeth. The metal tooth clamp or clamps serve to hold the partial denture securely in place within the patient's mouth and are designed to accomplish that function without detracting from the comfort of the partial denture.

It is therefore an object of the present invention to provide a partial denture with direct and positive attachments for securing the partial denture within the patient's mouth.

Another object of the present invention resides in the provision of a partial denture that includes one or more metal tooth clamps that directly and positively engage one or more existing teeth but which engage and clamp onto the patient's existing teeth in a fashion that results in comfort to the patient.

Another object of the present invention is to provide a partial denture that includes a denture base which is formed of a relatively hard acrylic material and which is provided with an existing tooth opening that is bordered on one side with an elastic retainer strip and on the other side with a metal filler panel and wherein both the elastic retainer strip and the metal filler parcel are integrally bonded or molded with the relatively hard acrylic material.

Another object of the present invent ion is to provide a partial denture that combines the benefit of a tooth supported partial denture with the addition of tissue-bone support.

Other objects and advantages of the present invention will become apparent and obvious from a study of the following description and the accompanying drawings which are merely illustrative of such invention.

DETAILED DESCRIPTION OF THE INVENTION

Figure 1:
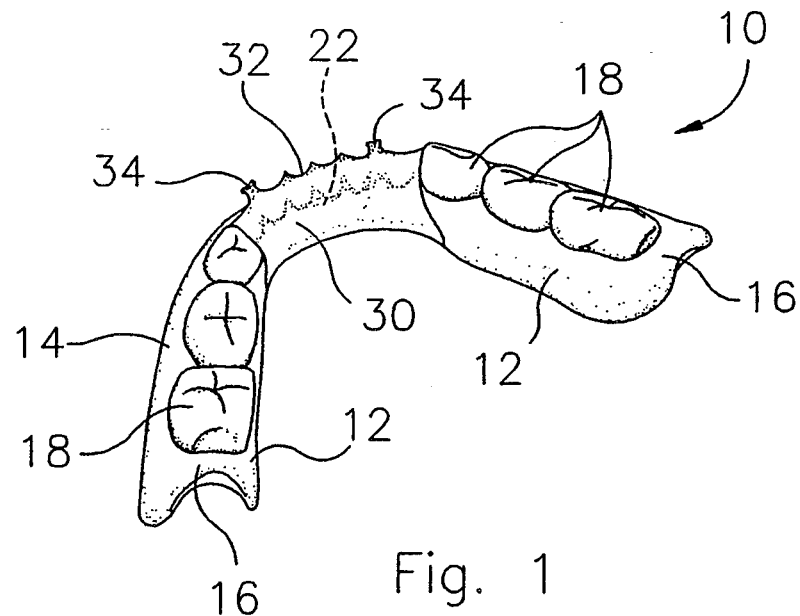
FIG. 1 is a perspective view of the partial denture of the present invention as viewed generally from the rear thereof.

With further reference to the drawings, the partial denture of the present invention is shown therein and indicated generally by the numeral 10. The partial denture 10 of the present invention includes a base or denture proper that is formed into a generally U-shape. The base of the partial denture includes a rear lingual flange 12 and a front buccal flange 14. Buccal flange 14 and lingual flange 12 curve upwardly towards the top portion to form a ridge 16. Secured on the ridge 16 is a series of artificial teeth 18.

The denture proper or the base of the denture forms a generally inverted U-shape gum cavity that is pre-shaped to conform to the gum of the patient. It follows that the gum cavity is shaped to allow the entire partial denture 10 to be properly seated on the patient's gums.

For each patient, the partial denture is designed to accommodate and accept existing healthy teeth, referred to by numeral 21, that the patient elects not to extract. To accommodate the patient's existing teeth, the partial denture 10 is provided with an elongated tooth opening 22 that is formed in a particular area on the ridge 16. As a practical matter, the partial denture 10 of the present invention contemplates that the elongated tooth opening 22 will in most cases be designed to accept two or more existing teeth 21. There may, however, be cases where it would be practical to form an existing tooth opening 22 that would be designed and sized to accommodate only one of the patient's existing teeth.

Turning to the structure of the partial denture 10, it should be pointed out that the base or denture proper is substantially constructed of a relatively hard acrylic material. As seen in the drawings, this relatively hard acrylic material forms the buccal flange, lingual flange and the ridge of the partial denture in and around the artificial teeth 18. But the makeup of the partial denture 10 in and around the tooth opening 22 varies from the relatively hard acrylic material. In this regard, formed about the front of the existing tooth opening 22 is an elastic retainer strip 28. The elastic retainer strip 28 is integrally molded or bonded with relatively hard acrylic material and tends to stretch across the front gum area in front of the patient's existing teeth 21 and acts to retain the partial denture within the patient's mouth. The top edge of the elastic retainer strip 28 is formed in a scalloped pattern so as to engage the base of the existing teeth in an area where the teeth join the patient's gum. More particularly, the scalloped upper edge of the retainer strip 28 tends to be pulled against the patient's front gum area and in so doing, the elastic retainer strip 28 tends to secure the entire partial denture in proper place within the patient's mouth.

It should be pointed out that the elastic retainer strip 28 is preferably bonded or molded to the relatively hard acrylic material in such a fashion that the opposite ends of the elastic retainer strip are essentially curved into an S-shape or other appropriate sweeping irregular shape so as to form an improved bonded joint between the elastic retainer strip 28 and the adjacent relatively hard acrylic material that forms the base of the denture. This approach of joining the elastic retainer strip will yield a greater connecting surface area and will in turn yield an improved and stronger joint between the elastic retainer strip 28 and the relatively hard acrylic material. For a more complete and unified understanding of a partial denture having an elastic retainer strip, one is referred to the disclosure found in U.S. Pat. No. 4,764,115 which is expressly incorporated herein by reference.

Figure 2:
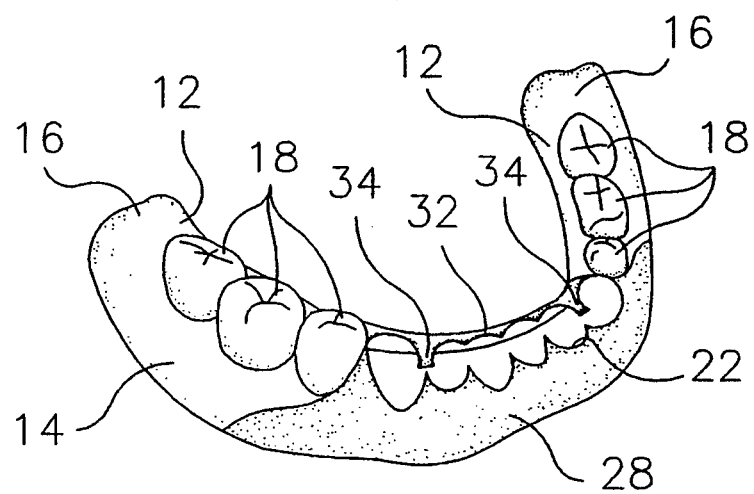
FIG. 2 is a fragmentary perspective view of a portion of the partial denture as viewed from the front.
Figure 3:
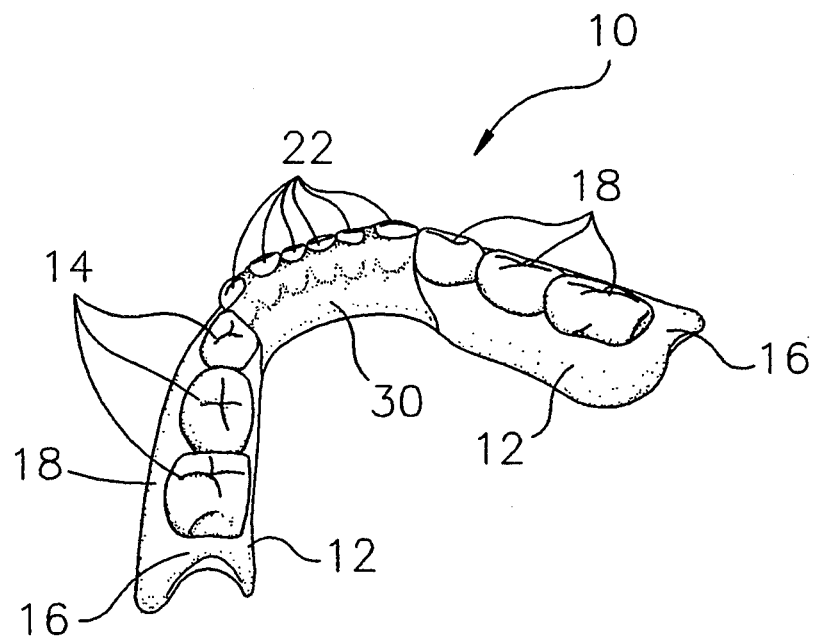
FIG. 3 is a perspective view of the partial denture of the present invention showing the same with the patient's existing teeth projecting through a portion of the partial denture.
Figure 4:
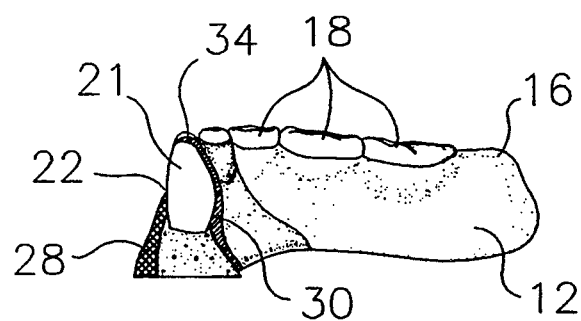
FIG. 4 is a transverse sectional view through the existing tooth opening of the partial denture and particularly illustrating the metal filler panel and its associated metal tooth clamp.

Formed on the opposite side of the elastic retainer strip 28 and extending around the existing tooth opening 22 is a metal filler panel 30. As seen in the drawings, the metal filler panel 30 essentially forms a part of the lingual flange 12 in the area adjacent the existing tooth opening 22. Metal filler panel 30 is bonded or otherwise integrally molded with the relatively hard acrylic material such that the entire denture 10 forms a single unit. As seen in the drawings, it is important to appreciate that the metal filler panel 30 actually lies directly adjacent the back of a portion of the patient's existing teeth. Consequently, the metal filler panel is actually shaped (crimped) to conform to a portion of the back of the patient's existing teeth. As seen in the drawings, the metal filler panel 30 includes an upper terminal edge 32 that forms a scallop shape. Note that the upper terminal edge 32 of the metal filler panel terminates and stops just short of the top of the patient's existing teeth (FIG. 2). But again as seen from the drawings, it is important to appreciate that the metal filler panel 30 actually abuts against and conforms to the shape of a portion of the patient's existing teeth.

In the embodiment illustrated in the drawings, there is provided a pair of metal clamps or rests 34 that project from the upper terminal edge 32 of the metal filler panel 30. Note that the clamps 34 extend upwardly and over and clamp downwardly onto one or more of the patient's existing teeth. For best results, it is appreciated that each clamp 34 is designed to clamp between two existing teeth. Therefore, each clamp 34 may actually engage a portion of two side-by-side teeth along the interface of those two teeth. Also, it may be appropriate to slightly grind or form a plateau in the teeth for the metal clamp 34 to engage.

Therefore, from the above discussion and from the drawings, it is seen that the metal clamps 34 provide a positive and direct attaching force for attaching the partial denture 10 in a secure position within the patient's mouth. In fact, the entire partial denture 10 is retained by the combined action of the elastic retainer strip 28 and the clamps 34 associated with the metal filler panel 30. The combined action of the metal clamps 34 and the elastic retainer strip 28 provide a positive and secure attaching feature for the partial denture 10 and the combined effect of the clamps 34 and the elastic retainer strip 28 provide the patient with a high degree of comfort while providing a sense of security.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An integral-acrylic metal partial denture comprising: a denture base including buccal and lingual flanges shaped to form a ridge for supporting a selected number of artifical teeth; an existing tooth opening formed in the ridge for permitting one or more existing teeth to project from the patient therethrough; the denture base being formed in part by a molded relatively hard acrylic material that is disposed adjacent the artifical teeth; an elastic retainer strip integrally formed with the relatively hard acrylic material and disposed along the buccal flange adjacent the existing tooth opening, the elastic strip engaging the gum of the patient in front of the existing opening and bearing against the gum of the patient when the denture base is disposed within the patient's mouth; a metal filler panel integrally formed with the relatively hard acrylic material and disposed along the lingual flange adjacent the existing tooth opening, the metal filler panel having an upper terminal edge; and at least one metal tooth clamp extending from the upper terminal edge of the metal filler panel and extending over at least one existing tooth of the patient and engaging and clamping a top portion of the existing tooth so as to assist in securing the entire partial denture in the patient's mouth.

2. The partial denture of claim 1 wherein the denture includes a pair of laterally spaced metal tooth clamps that extend from the terminal edge of the metal filler panel over the existing teeth and engage a top portion of the same for assisting in retaining the partial denture within the patient's mouth.

3. The partial denture of claim 1 wherein the metal tooth clamp is specifically directed to extend between two existing teeth and to engage a top portion of the two existing teeth in order to retain the partial denture within the patient's mouth.

4. A method of forming a partial denture comprising: forming a denture base of a relatively hard acrylic material and placing a selected number of artifical teeth on the denture base; forming an existing tooth opening in the ridge of the denture base for accepting one or more teeth from a patient; integrally molding an elastic strip of material in the buccal flange area of the denture base adjacent the existing tooth opening such that the elastic strip of material tends to engage the gum of the patient in the area adjacent the existing tooth openings when the denture assumes an appropriate position in the patient's mouth; integrally implanting a metal filler panel in the lingual flange adjacent the existing tooth opening; and extending at least one metal tooth clamp from an upper terminal edge of the metal filler panel and directing the tooth clamp over the existing tooth opening such that it will engage a top portion of an existing tooth of a patient projecting through the opening such that the tooth clamp will assist in retaining the partial denture within the patient's mouth.

5. The method of claim 4 including the step of extending a pair of laterally spaced metal tooth clamps from the upper terminal edge of the metal filler panel so as to engage the existing teeth of a patient at two spaced apart points.

6. The method of claim 4 including the step of grinding a top portion of a patient's existing tooth to form a clamping area and extending the metal tooth clamp such that a terminal end portion of the same engages the ground portion of the patient's tooth so as to assist in retaining the partial denture within the patient's mouth.

* * * * *